(12) United States Patent
Jenney

(10) Patent No.: US 12,102,823 B2
(45) Date of Patent: Oct. 1, 2024

(54) DEVICE, SYSTEM, AND METHOD FOR DELIVERY OF AN IMPLANTABLE CARDIAC LEAD AND ASSOCIATED ACTIVE AGENT DELIVERY COMPONENT

(71) Applicant: Pacesetter, Inc., Sylmar, CA (US)

(72) Inventor: Christopher Jenney, Valencia, CA (US)

(73) Assignee: Pacesetter, Inc., Sylmar (CA)

( * ) Notice: Subject to any disclaimer, the term of this patent is extended or adjusted under 35 U.S.C. 154(b) by 766 days.

(21) Appl. No.: 17/121,994

(22) Filed: Dec. 15, 2020

(65) Prior Publication Data

US 2021/0187285 A1    Jun. 24, 2021

Related U.S. Application Data

(60) Provisional application No. 62/949,601, filed on Dec. 18, 2019.

(51) Int. Cl.
*A61N 1/05*       (2006.01)
*A61N 1/375*     (2006.01)

(52) U.S. Cl.
CPC ......... *A61N 1/0575* (2013.01); *A61N 1/0568* (2013.01); *A61N 1/37512* (2017.08)

(58) Field of Classification Search
CPC . A61N 1/0575; A61N 1/0568; A61N 1/37512
See application file for complete search history.

(56) References Cited

U.S. PATENT DOCUMENTS

| | | | | |
|---|---|---|---|---|
| 5,447,533 | A * | 9/1995 | Vachon | A61N 1/056 600/374 |
| 2003/0073972 | A1* | 4/2003 | Rosenman | A61M 37/0069 604/502 |
| 2019/0134413 | A1* | 5/2019 | Mar | A61N 1/37518 |

* cited by examiner

*Primary Examiner* — Joseph M Dietrich
(74) *Attorney, Agent, or Firm* — Dean D. Small; The Small Patent Law Group, LLC

(57) ABSTRACT

Delivery of implantable active agent delivery components includes implanting a distal lead end of a lead into tissue at an implantation site. A delivery stylet is then inserted through a lead lumen of the lead. The delivery stylet includes a stylet body having a distal stylet end and an active agent delivery component detachably coupled to the distal stylet end. The active agent delivery component is inserted into the tissue at the implantation site by extending the distal stylet end of the delivery stylet from a distal lead end of the lead such that the active agent delivery component is inserted into the tissue at the implantation site. The active agent delivery component is then detached within the tissue at the implantation site and the delivery stylet may be retracted and removed from the lead lumen.

19 Claims, 14 Drawing Sheets

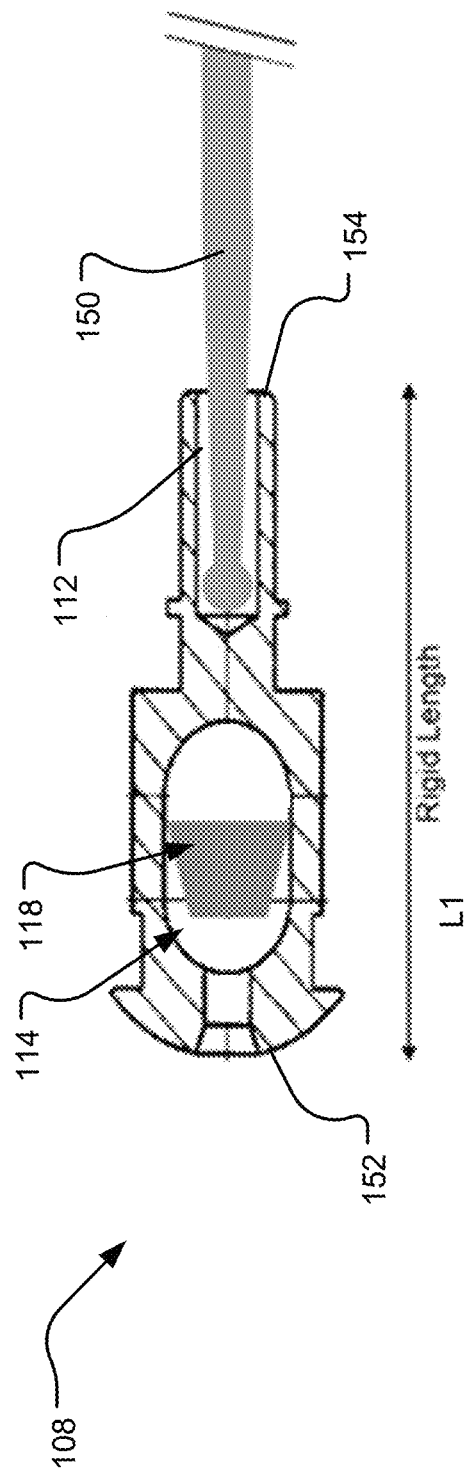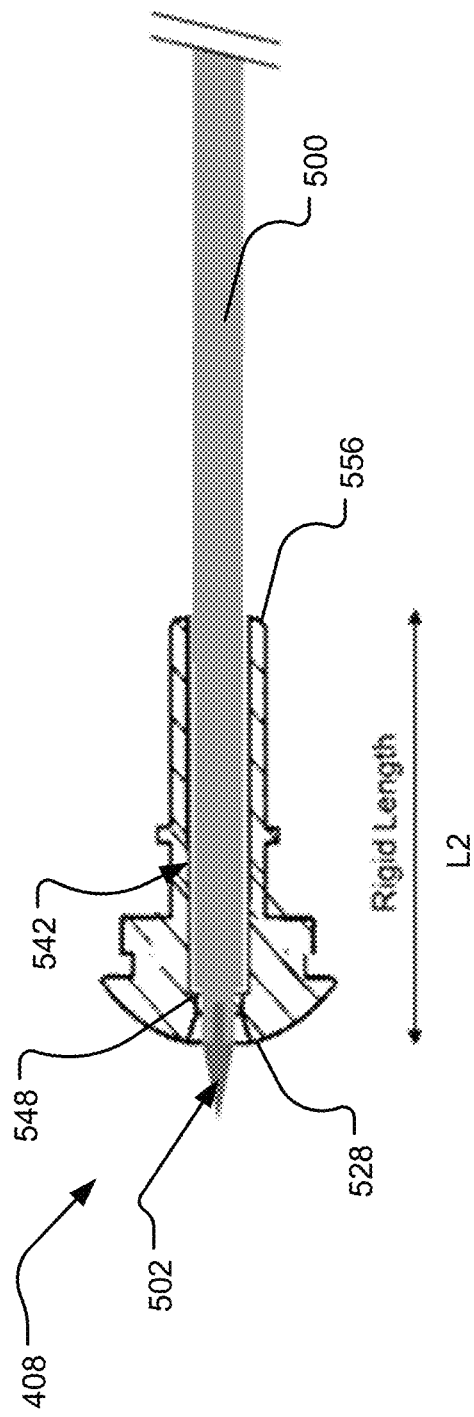
FIG. 5A
FIG. 5B

```
                    ┌─────────────────────────────────────────────────────┐
   1100             │  IMPLANT DISTAL LEAD END OF LEAD BODY INTO THE TISSUE │
      ↘            │                        1102                          │
                    └─────────────────────────────────────────────────────┘
                                              │
                                              ▼
                    ┌─────────────────────────────────────────────────────┐
                    │        INSERT DELIVERY STYLET THROUGH LEAD LUMEN     │
                    │                        1104                          │
                    └─────────────────────────────────────────────────────┘
                                              │
                                              ▼
                    ┌─────────────────────────────────────────────────────┐
                    │  EXTEND DISTAL STYLET END FROM DISTAL LEAD END TO    │
                    │  IMPLANT ACTIVE AGENT DELIVERY COMPONENT IN TISSUE   │
                    │              AT IMPLANTATION SITE                    │
                    │                        1106                          │
                    └─────────────────────────────────────────────────────┘
                                              │
                                              ▼
                    ┌─────────────────────────────────────────────────────┐
                    │   DETACH ACTIVE AGENT DELIVERY COMPONENT FROM        │
                    │                DELIVERY STYLET                       │
                    │                        1108                          │
                    └─────────────────────────────────────────────────────┘
                                              │
                                              ▼
                    ┌─────────────────────────────────────────────────────┐
                    │         RETRACT AND REMOVE DELIVERY STYLET           │
                    │                        1110                          │
                    └─────────────────────────────────────────────────────┘
```

*FIG. 11*

DEVICE, SYSTEM, AND METHOD FOR DELIVERY OF AN IMPLANTABLE CARDIAC LEAD AND ASSOCIATED ACTIVE AGENT DELIVERY COMPONENT

CROSS-REFERENCE TO RELATED APPLICATION

This application claims the benefit of U.S. Provisional Application No. 62/949,601 filed Dec. 18, 2019, which is hereby incorporated by reference in its entirety.

TECHNICAL FIELD

The present disclosure is directed to implantable medical devices such as, for example, cardiac rhythm management pacing and defibrillation leads. More specifically, the present disclosure is directed to systems and methods for implantation of devices for delivery of active pharmaceutical ingredients at implantation sites of implantable medical devices.

BACKGROUND

Implantable cardiac rhythm management devices (ICRMD), such as pacemakers with implantable cardiac leads and leadless pacemakers, are generally used for pacing and/or defibrillation of the heart to address various cardiac pathologies. Such devices may include implantable elements may further employ components for delivering an active agent to implantation sites of the implantable elements. In the case of implantable leads and leadless pacemakers, such delivery components may include monolithic controlled release device (MCRD), which are generally positioned near the distal tip of the implantable lead or leadless pacemaker. The MCRD carries an active agent and is positioned such that the MCRD is held in close proximity to, if not in actual physical contact with, the cardiac tissue at the implantation site following implantation of the lead. Following implantation of the lead, the MCRD elutes the active agent (which may include but is not limited to anti-inflammatory medications, steroids, and other therapeutic agents) to the surrounding tissue. In pacing applications, for example, the active agent may be selected to reduce myocardial inflammation at the implantation site in order to keep pacing thresholds low, thereby improving operation and efficiency of the implanted medical device.

Accordingly, there is a need in the art for electrode designs, MCRD designs, and lead designs, generally, that improve MCRD yield, and provide consistent delivery of the active agent at the implantation site.

SUMMARY

In one aspect of the present disclosure, a system for implanting an implantable medical device lead is provided. The system includes a lead including a lead body defining a lead lumen and a distal lead end adapted to engage tissue, the lead lumen extending through the distal lead end. The system further includes a delivery stylet insertable through the lead lumen. The delivery stylet includes a stylet body having a distal stylet end and an active agent delivery component detachably coupled to the distal stylet end. The delivery stylet is insertable through the lead lumen such that the distal stylet end protrudes from the distal lead end, thereby enabling insertion of the active agent delivery component into the tissue to which the distal lead end is engaged.

In certain example implementations the lead is a cardiac pacing lead and the distal lead end further includes a pacing electrode.

In certain example implementations the delivery stylet may include a first feature configured to abut a second feature disposed within the lead lumen. By doing so, each of distal movement of the delivery stylet within the lead lumen and protrusion of the delivery stylet from the distal lead end may be limited. In certain implementations, the first feature may be a distally facing surface of the delivery stylet while the second feature may be a proximally facing surface disposed within the lead lumen.

In certain example implementations the delivery stylet may include an outer sleeve and an inner stylet. The inner stylet is movable within the outer sleeve and includes the distal stylet end and the active agent delivery component.

In certain example implementations the stylet body defines a stylet lumen configured to receive at least one of a push tool for applying a force on the active agent delivery component and a retention tool extending through the stylet body and coupled to the active agent delivery component.

In certain example implementations the active agent delivery component may include a steroid.

In another aspect of the present disclosure, a method of delivering active agents to tissue at an implantation location of a lead is provided. The lead includes a lead body defining a lead lumen and a distal lead end engaging the tissue at the implantation location, the lead lumen extending through the distal lead end. The method includes the steps of inserting a delivery stylet through the lead lumen, the delivery stylet including a stylet body having a distal stylet end and an active agent delivery component detachably coupled to the distal stylet end. The method further includes extending the distal stylet end from the distal lead end such that the active agent delivery component is inserted into the tissue at the implantation location. The method also includes detaching the active agent delivery component from the distal stylet end and within the tissue at the implantation location.

In certain example implementations the delivery stylet includes a distally facing surface and the lead comprises a proximally facing surface disposed within the lead lumen. In such implementations, extending the distal stylet end from the distal lead end comprises abutting the distally facing surface with the proximally facing surface such that the active agent delivery component is extended a predetermined distance from the distal lead end.

In certain example implementations the delivery stylet may include a distally facing surface and the lead may include a proximally facing surface disposed within the lead lumen. The delivery stylet may further include an outer tubular body including the distally facing surface and an inner stylet movable within the outer tubular body, the inner stylet including the distal stylet end. In such implementations, extending the distal stylet end from the distal lead end may include moving the inner stylet distally relative to the outer tubular body after abutting the distally facing surface and the proximally facing surface.

In certain example implementations detaching the active agent delivery component from the distal stylet may include at least one of retracting the stylet body after insertion of the active agent delivery component in the tissue at the implantation site, inserting a push tool through the stylet body to apply a proximal force on the active agent delivery component, retracting a retention tool extending through the stylet body and coupled to the active agent delivery component, and dissolving a bond between the active agent delivery component and the distal stylet end.

In certain example implementations the method further includes, prior to inserting the delivery stylet through the lead lumen, implanting the distal lead end into the tissue at the implantation site.

In certain example implementations the active agent delivery component includes a steroid.

In still another aspect of the present disclosure, a stylet for use in delivery of active agents to an implantation site of an implantable medical lead is provided. The stylet includes a stylet body having a distal stylet end and an active agent delivery component detachably coupled to the distal stylet end.

In certain example implementations the stylet body further includes an outer sleeve and an inner stylet movable within the outer sleeve, the inner stylet comprising the distal stylet end and the active agent delivery component.

In certain example implementations the stylet body includes a distally facing surface disposed proximal the distal stylet end.

In certain example implementations the active agent delivery component includes a radiopaque marker.

In certain example implementations the active agent delivery component is coupled to the distal stylet end by a dissolvable bond.

In certain example implementations the stylet body defines an inner lumen and the active agent delivery component is detachable from the distal stylet end by inserting an elongate tool through the inner lumen and applying a distal force on the active agent delivery component.

In certain example implementations the stylet body defines an inner lumen and further includes an elongate retention tool disposed within the inner lumen and coupled to the active agent delivery component, the active agent delivery component being detachable from the distal stylet end by retracting the elongate retention tool.

BRIEF DESCRIPTION OF THE DRAWINGS

FIGS. 5A and 5B are, respectively, a cross-sectional side view of a conventional electrode with a distal chamber for housing an active agent delivery component, and a cross-sectional view of an electrode with a lumen fully passing through the electrode.

FIG. 11 is a flowchart showing an exemplary method of delivering an implantable cardiac lead and an active agent delivery component into tissue at an implantation site.

DETAILED DESCRIPTION

The following discussion is directed to implantable medical devices, such as cardiac rhythm management devices (ICRMD), employing active agent delivery components, such as monolithic controlled release devices (MCRD), that carry an active agent. In certain example applications, the active agent delivery component may be an MCRD formed from a blend of steroid powder (or other active agent powder) and silicone rubber. Also in certain example applications, the ICRMD may be in the form of an implantable cardiac lead for pacing, sensing, and/or defibrillation. As discussed below in further detail, such leads may be configured for passive or active fixation.

Figure 1A:
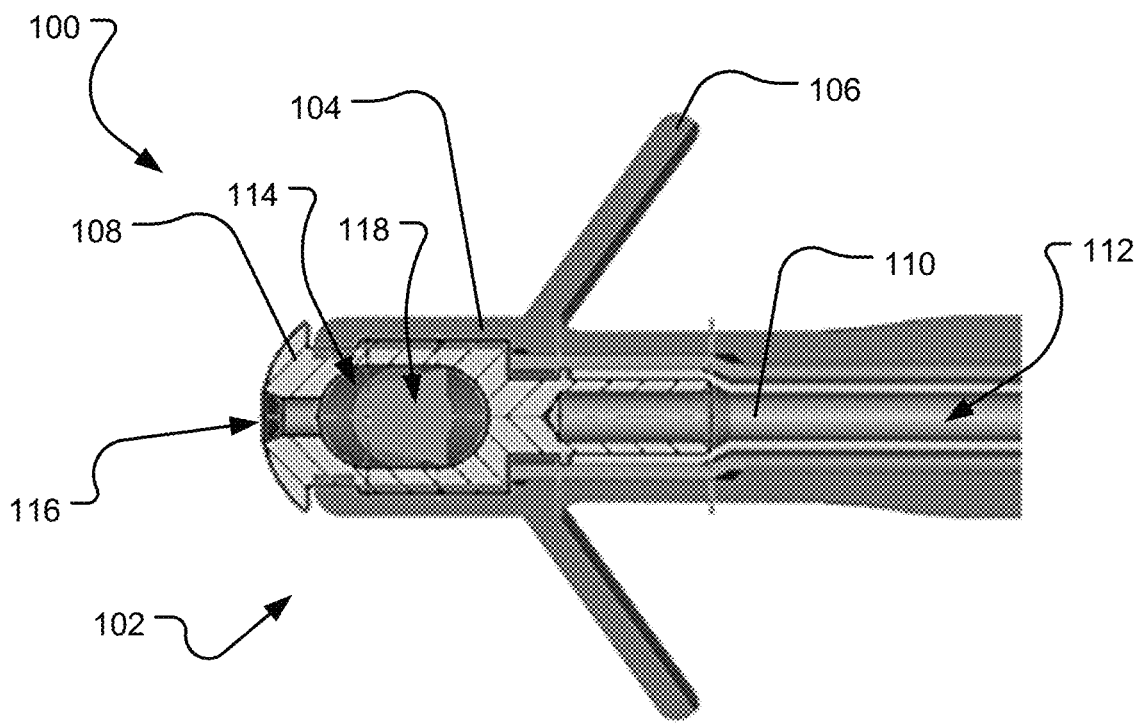
FIG. 1A is a cross-sectional side view of a distal region of a lead including an electrode and an example monolithic controlled release device (MCRD) positioned in a chamber of the electrode.

Conventionally, as seen in FIG. 1A, which is a cross-sectional side view of a distal region 102 of an implantable lead 100, a tubular lead body 104 (which may include outwardly extending fixation members 106 in the form of tines) partially encases an electrode 108 which extends from the end of the tubular lead body 104. The electrode 108 is physically and electrically connected to a conductor 110, e.g., a tubular coiled conductor, that extends proximally along the length of the implantable lead 100. As seen in FIG. 1A, in at least certain conventional applications, the electrode 108 includes a proximal opening 112 forming a lumen that continues through the coiled conductor 110. The electrode 108 also includes a chamber 114 that opens to a distal opening 116. In conventional applications, an MCRD 118 is generally housed in the chamber 114.

Figure 1B:
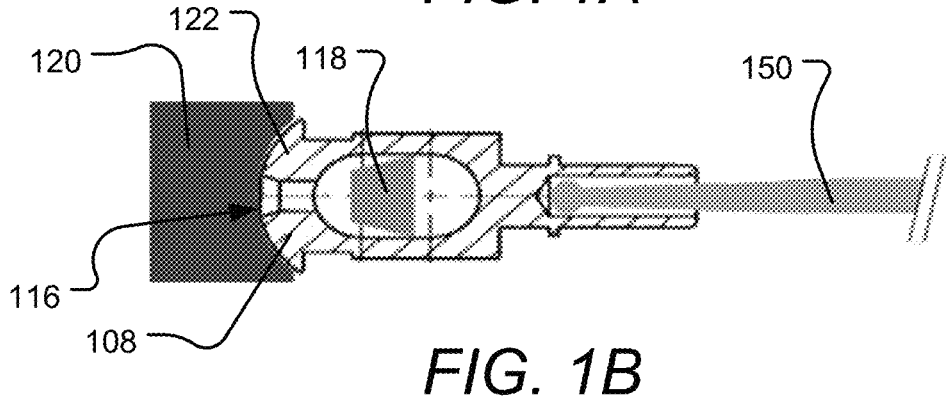
FIG. 1B is a cross-sectional side view of the electrode 108 abutting the myocardium of a heart with a stylet used to advance the electrode.

The distal region 102 of the lead 100 is delivered to the myocardium 120 of the heart, as seen in FIG. 1B, which shows the electrode 108 by itself in a cross-sectional side view abutting the myocardium 120 and being delivered using a placement stylet 150. In this position, the fixation members 106 (shown in FIG. 1A) would be anchored to the epicardium (not shown) or similar cardiac tissue. As seen in FIG. 1B, a distal tip 122 of the electrode and the distal opening 116 may be made to contact the myocardium 120.

Figure 1C:
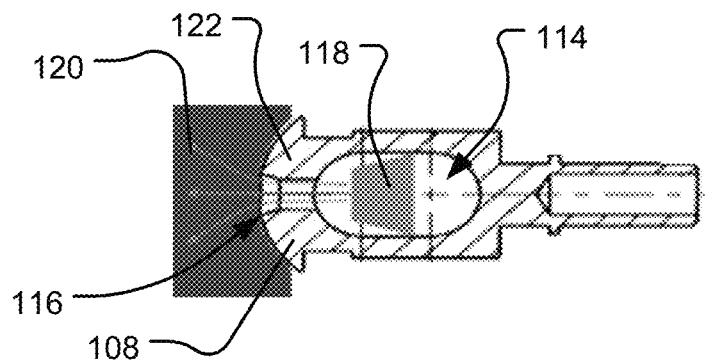
FIG. 1C is a cross-sectional side view of the electrode abutting the myocardium of the heart showing an active agent eluting from the MCRD and interfacing with blood and tissue from the myocardium.

Following implantation, blood and other bodily fluids infiltrate the chamber 114, as seen in FIG. 1C, which is a cross-sectional side view of the electrode 108 abutting the myocardium 120, which causes the release of an active agent from the MCRD 118 into the tissue and blood. The active agents may be chosen for various purposes; however, in at least some implementations, the active agents may be chosen to reduce inflammation of the tissue disturbed by the introduction of the electrode 108, fixation members 106, and the lead 100.

Various disadvantages are associated with conventional techniques in which the MCRD 118 is housed in the chamber 114. For example, if replacement of the MCRD 118 is required (e.g., in conjunction with repositioning the lead after an initial implantation) the lead 100 must generally be fully removed from the heart in order to replace the MCRD 118. Then, following replacement of the MCRD 118, the lead may be reinserted and implanted in the tissue. Alternatively, in at least certain conventional applications in which the MCRD 118 is not removable, the entire lead must generally be replaced.

As discussed in detail below, implementations of the present disclosure facilitate delivery of an active agent delivery component, such as an MCRD, directly into tissue at an implantation site. Such implementations generally include a lead that may be implanted at an implantation site and that include a lumen extending from a proximal end through a distal tip of the lead. Following implantation of the lead, a delivery stylet having an MCRD or similar active agent delivery component disposed on a distal end may be inserted through the lumen of the lead such that the active agent delivery component extends through the distal tip of the lead. Such extension enables the MCRD to be inserted/implanted directly into the tissue at the implantation site.

Notably, implementations of the present disclosure facilitate delivery of additional MCRDs or similar active agent delivery components without full removal of the lead. For example, following initial implantation, an additional MCRD or active agent delivery component may be delivered through the lumen of the lead without requiring detachment and removal of the lead from the implantation site. Similarly, if the lead tip is to be repositioned, the lead may be detached from the initial implantation site and implanted at a second implantation site without substantially removing the lead from the patient and/or the lead tip from an area of interest (e.g., a heart chamber). Following implantation at the second site, a new MCRD or other active agent delivery component may be delivered through the lead for implantation at the second implantation site.

Moreover, without requiring a dedicated chamber for housing an MCRD at a lead tip, the rigid length of the lead tip may be shortened, resulting in a more flexible and more maneuverable lead.

All of the foregoing combines to provide improved active agent delivery, easier modification to lead placement, and easier access to the implantation site, among other things.

I. Implantable Cardiac Lead Including an MCRD

Figure 2A:
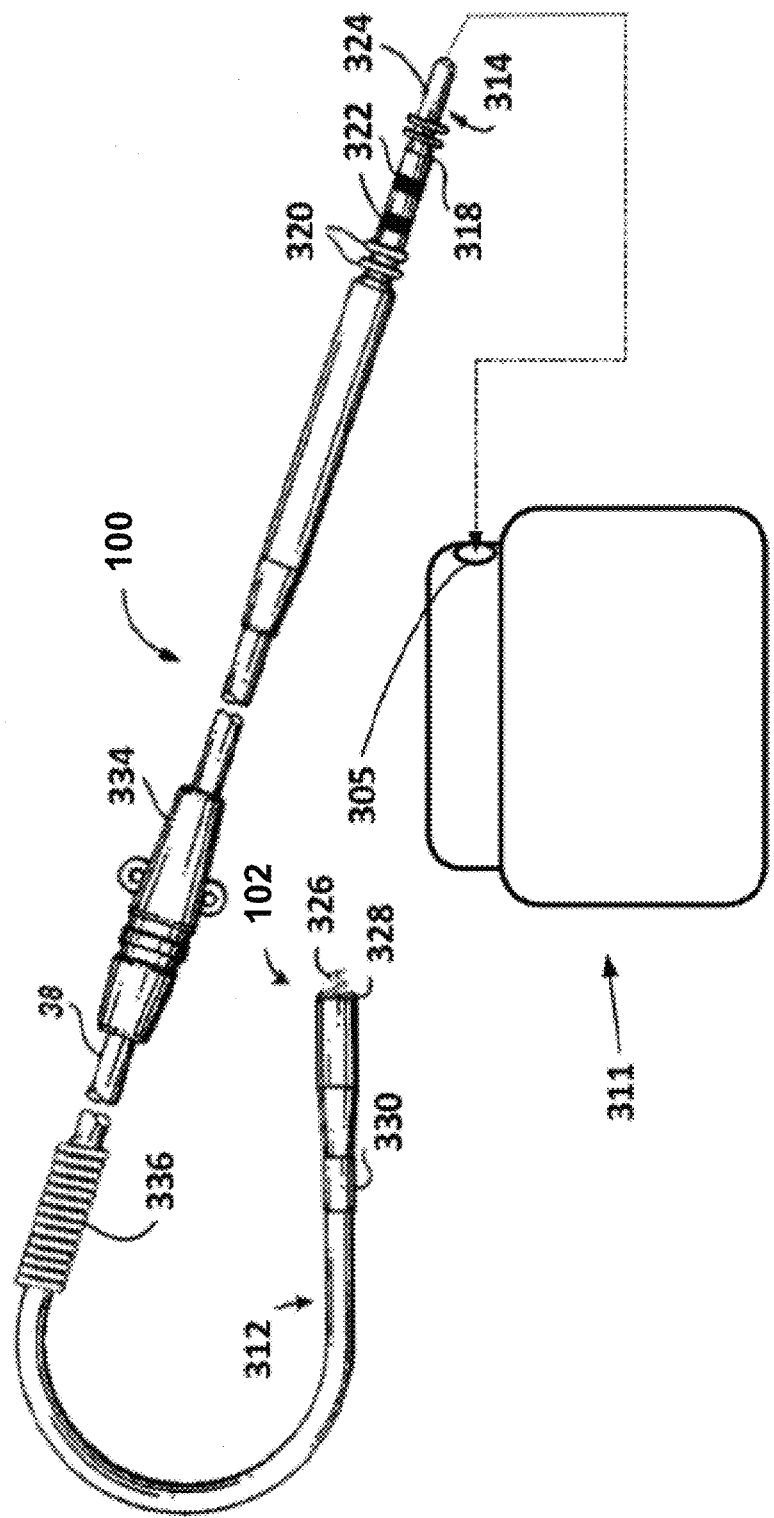
FIG. 2A is a plan view of a lead in accordance with the present disclosure that is connectable with a pulse generator, wherein an active fixation anchor of the lead is shown in an extended or deployed state.

In some instances, aspects of the present disclosure may include an implantable MCRD for use with an implantable cardiac lead. A non-limiting example of such a lead 100 is depicted in FIG. 2A, which is a plan view of an embodiment of a lead 100 that is connectable with a pulse generator 311. As illustrated in FIG. 2A, in one embodiment, the lead 100 has a fixation anchor 326, which is shown in an extended or deployed state. In general, the fixation anchor 326 implants into tissue to fix a distal end of the lead 100 therein. The fixation anchor 326 may be active such that it also provides pacing and/or sensing functionality or passive, such that the fixation anchor 326 anchors the lead to the tissue only. In implementations including a passive fixation anchor, pacing and/or sensing is generally facilitated by one or more additional electrodes disposed at a distal end of the lead 100. Fixation member 106 of FIG. 1A, for example, is a passive fixation member 106 in which electrode 108 provides sensing/pacing functionality.

The lead 100 may be designed for intravenous insertion and contact with the endocardium, or the lead 100 may be designed for placement external to the heart, for example, in the pericardial space. As indicated in FIG. 2A, the lead 100 is provided with an elongated lead body 312 that extends between a proximal region 314 and distal region 102 of the lead 100.

The proximal region 314 of the lead 100 includes a connector assembly 318, which may include sealing rings 320 and at least one or more electrical connectors in the form of ring contacts 322, pin contacts 324, and the like. The connector assembly 318 is configured to be plugged into a receptacle 305 of the pulse generator 311, the sealing rings 320 forming a fluid-tight seal to prevent the ingress of fluids into the receptacle 305 of the pulse generator 311. When the connector assembly 318 is plugged into the pulse generator receptacle 305, the contacts 322, 324 electrically connect with the circuitry of the pulse generator such that electrical signals can be administered and sensed by the pulse generator via the electrical pathways of the lead 100.

The connector assembly 318 is constructed using known techniques and is preferably fabricated from silicone rubber, polyurethane, silicone-polyurethane-copolymer ("SPC"), or other suitable polymers. The electrical contacts 322, 324 are preferably fabricated of stainless steel or other suitable electrically conductive material that is biocompatible.

As can be understood from FIG. 2A, in some embodiments, the distal region 102 of the lead 100 includes the fixation anchor 326 distally extending from a distal tip end 328 of the lead 100. In certain implementations, the fixation anchor 326 may be transitioned between a retracted/non-deployed state and a deployed state, with FIG. 2A illustrating the fixation anchor in the deployed state. The fixation anchor 326 may be transitioned to the non-deployed state via retraction of the anchor 326 into the confines of the distal region 316 of the lead 100. Although illustrated in the form of a helical wire/coil, the fixation anchor 326 may have any suitable shape and configuration that permits anchoring to tissue and, in implementations in which fixation anchor 326 is active, communication of electrical signals (e.g., pacing signals, sensing signals) to and/or from the tissue.

As previously noted, when active, the fixation anchor 326 is configured to act as an electrode in addition to providing fixation to heart tissue. Where the anchor 326 is also configured to act as an electrode, depending on the dictates of the pulse generator 311, the anchor 326 may be employed for sensing electrical energy and/or administration of electrical energy (e.g., pacing). The anchor 326 is electrically coupled to the pin contact 324 of the connector assembly 318 via an electrical conductor extending through the lead body 312 and the connector assembly 318. In implementations in which the anchor 326 is passive, similar electrical connections may be established between an electrode at or near the distal tip end 328 of the lead and the various components of the connector assembly 318.

In certain implementations, the distal region 102 of the lead 100 may include a ring electrode 330 proximally offset from the distal tip end 328 of the lead 100. Depending on the dictates of the pulse generator 311, this ring electrode 330 may be employed for sensing electrical energy and/or administration of electrical energy (e.g., pacing). The ring electrode 330 is electrically coupled to one of the ring contacts 322 of the connector assembly 318 via an electrical conductor extending through the lead body 312 and the connector assembly 318.

As depicted in FIG. 2A, the lead 100 may include a fixation sleeve 334 slidably mounted around the lead body 312. Among other things, the fixation sleeve 334 serves to stabilize the pacing lead 100 at the site of venous insertion.

Where the lead 100 is equipped for defibrillation as shown in FIG. 2A, a shock coil 336 may also be supported on the lead body 312 proximal the ring electrode 330 and distal the fixation sleeve 334. The shock coil 336 is electrically coupled to one of the ring contacts 322 of the connector assembly 318 via electrical conductors extending through the lead body 312.

The foregoing description of the lead 100 is only as an example only and should not be considered limiting to the present disclosure. The present disclosure is not limited to any specific leads or implantable medical devices provided that the lead facilitates the active agent delivery systems and methods discussed below. Stated differently, leads and implantable devices in accordance with the present disclosure may vary from the specific example discussed above and may still be within the scope of this disclosure and, more specifically, the disclosure related to active agent delivery systems and methods provided below. Among other things, the design of the anchor, the placement and configuration of the electrical components, the type of the implantable device (e.g., pulse generator), lead construction, and other aspects of the system may vary from that which is disclosed above while still being within the scope of this disclosure.

Figure 2B:
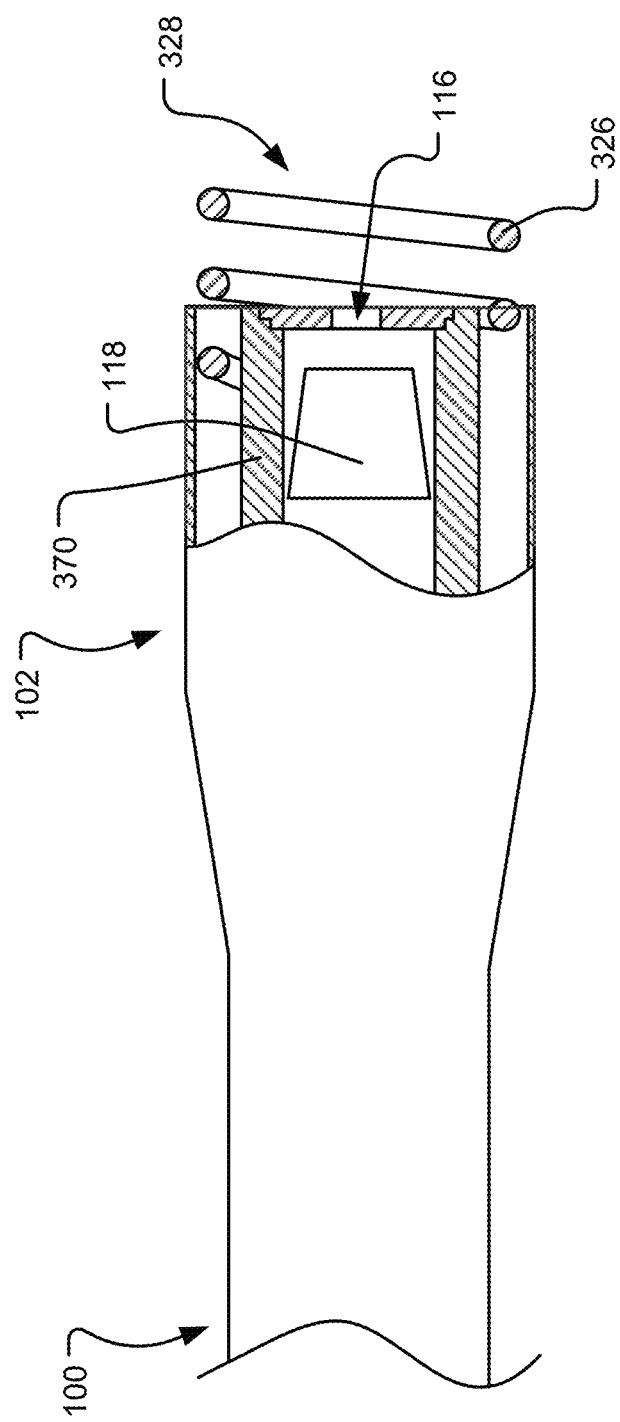
FIG. 2B is a partial cutaway view of the distal region of the implantable cardiac lead of FIG. 2A, the distal region having a helical active fixation anchor.

Referring now to FIG. 2B, an enlarged partial cutaway view of the distal region 102 of the implantable lead 100 of FIG. 2A is provided that illustrates conventional placement of the MCRD 118 within the distal region 102 of the implantable lead 100. As illustrated in FIG. 2B, the MCRD 118 is conventionally positioned within a housing structure 370 proximal the distal tip end 328 and the fixation anchor 326. As discussed above in the context of FIGS. 1A-1C, following implantation of the fixation anchor 326, blood and other bodily fluids infiltrate the chamber 114 through a distal opening 116, which causes the release of an active agent from the MCRD 118 into the adjacent tissue and blood.

II. Implantable Cardiac Lead System Employing an Implantable Active Agent Delivery Component, a Delivery Stylet, and a Pass-Through Lead Tip A. Delivery Stylets To begin a detailed discussion of an example cardiac lead and active agent delivery system, reference is made to FIG. 3, which depicts a side view of a delivery stylet 500 coupled to an active agent delivery component. For purposes of this disclosure, the active agent delivery component is also and interchangeably referred to as an MCRD 502. As can be understood from FIG. 3, the delivery stylet 500 may include a stylet body 504 in the form of a cylindrical rod, a distal stylet end 506 for coupling with the MCRD 502, and shoulder 508 having a distal facing surface 510. The distal stylet end 506 may include a cylindrical body of a lesser diameter than a diameter of the stylet body 504. The shoulder 508 joins the cylindrical bodies of different diameters of the distal stylet end 506 and the stylet body 504. The distal stylet end 506 may include a distal bore 512 for receiving a portion of the MCRD 502. The distal bore 512 may be defined centrally within the cylindrical body of the distal stylet end 506.

Figure 3:
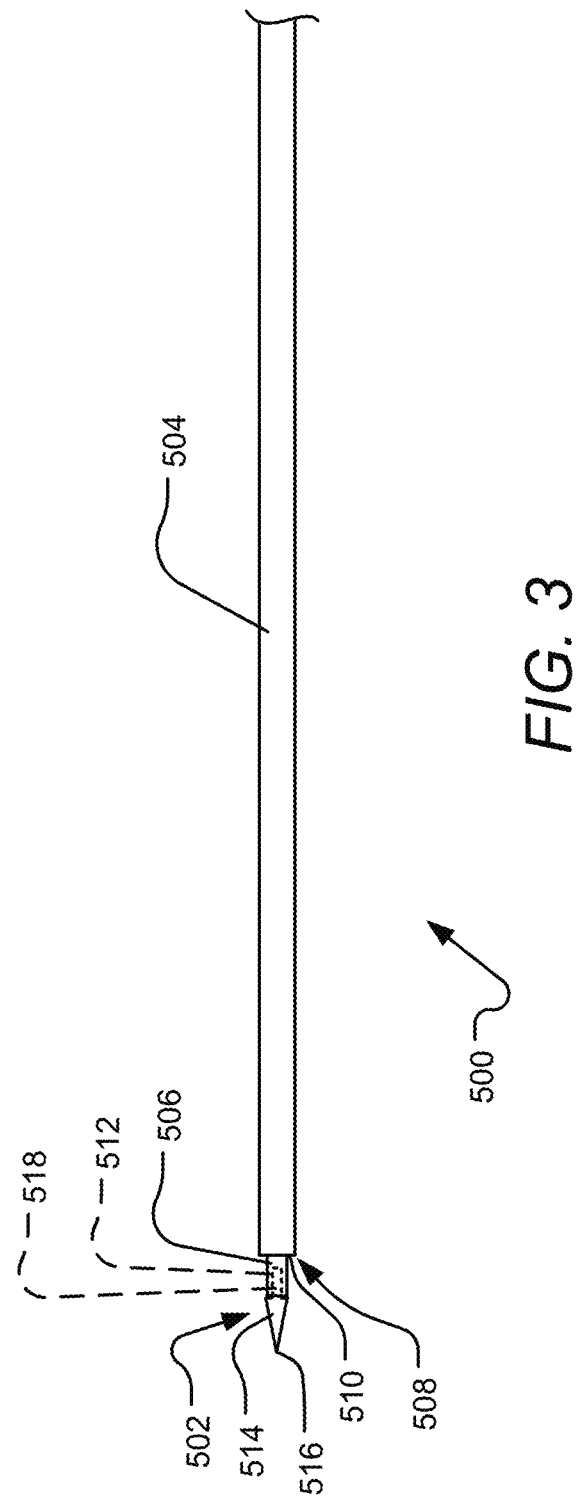
FIG. 3 is a side view of a delivery stylet coupled with an active agent delivery component, such as an MCRD.

As seen in FIG. 3, in one implementation of the present disclosure, the MCRD 502 may include a distal head 514 in the form of a conical distal surface that terminates at a piercing tip 516. And a tang 518 extending proximally from the distal head 514 and that is received in the distal bore 512 of the distal stylet end 506 of the delivery stylet 500. Various shapes and configurations of the MCRD 502, as well as mechanisms to facilitate coupling and release of the MCRD 118 to/from the distal stylet end 506, are contemplated and will be described subsequently.

Figure 6A:
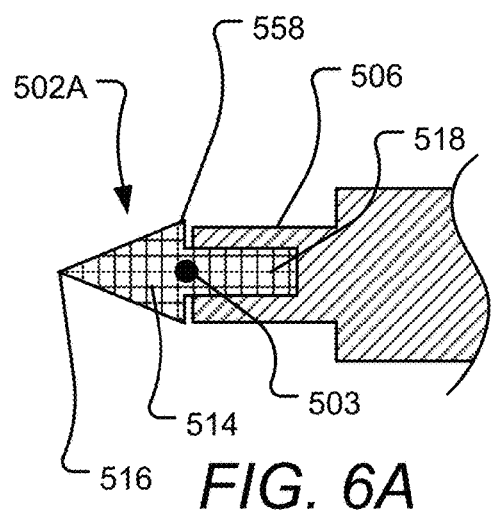
FIGS. 6A-6F are cross-sectional side views of various shapes and configurations of active agent delivery components in accordance with the present disclosure.
Figure 6D:
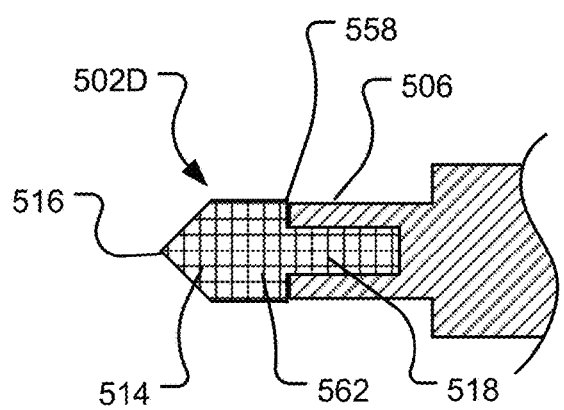

In certain instances, the MCRD 502 may be injection molded from a blend of resorbable polymer and an active agent. In at least certain implementations, the active agent may be a steroid (e.g. dexamethasone acetate or dexamethasone). Resorbable polymers include polylactic acid (PLA), polyglycolic acid (PGA), and polycaprolactone (PCL) or a related co-polymer. By controlling the ratio of monomers in the polymer, the resorption time can be well controlled, allowing customization of active agent release to optimize the physiological effect. The resorbable polymers may be relatively rigid and may be formulated to be highly compatible with dexamethasone derivatives or other steroids so that a homogenous and highly concentrated blend can be achieved. Also, these polymers can be injection molded with high precision, allowing MCRD 502 designs smaller than conventional designs, such as the MCRD 118 illustrated in FIG. 2B. In at least certain other implementations, the resorbable polymer may be substituted with an alternative material that is biocompatible and may be blended or impregnated with an active ingredient for subsequent release when exposed to tissue or bodily fluid. In at least certain implementations, the MCRD 502 may include a radiopaque marker. For example, and without limitation, the radiopaque marker may include a bead, ring, strip, stick, or similar object formed of a radiopaque material and embedded or coupled to a body of the MCRD 502. Alternatively, the MCRD 118 may be molded, at least in part, using a material having radiopaque particles, powder, or other similar material mixed in. An example of a radiopaque bead 503 is illustrated in FIG. 6A, which is discussed below in further detail.

B. Delivery Using a Lead Tip with Passive Fixation

Figure 4A:
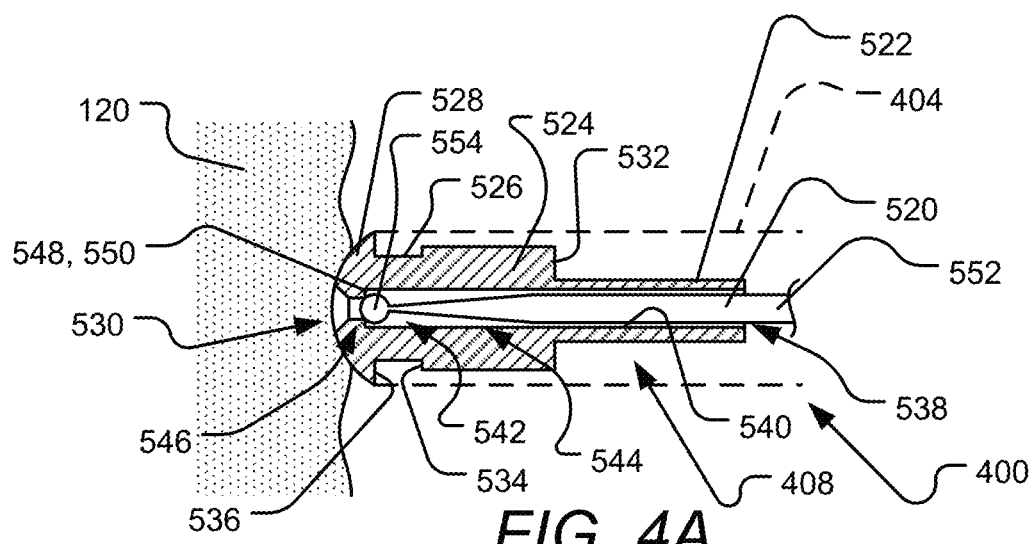
FIGS. 4A-4C are, respectively, cross-sectional side views of an electrode positioned against the myocardium with a placement stylet positioned therein, a delivery stylet positioned therein, and the active agent delivery component positioned within the myocardium with the delivery stylet retracted.

FIG. 4A is a cross-sectional side view of an electrode 408 of a lead 400 abutting the myocardium 120 with a placement stylet 520 positioned therein. The delivery stylet 500 and MCRD 502 of FIG. 3 may be used with the lead tip or electrode 408 illustrated in FIG. 4A. Although a passive fixation member is not included in FIGS. 4A-4C for clarity, the lead 400 may include a passive fixation member, such as the fixation members 106 of FIG. 1A for purposes of engaging and coupling the distal portion of the lead to the myocardium 120 and maintaining the electrode 408 in contact with the myocardium 120.

Figure 4B:
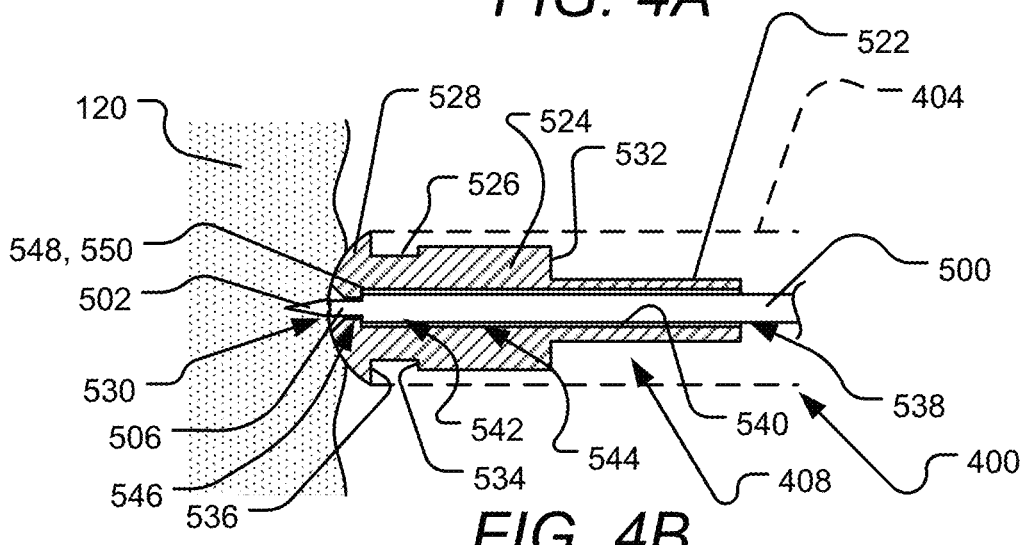
Figure 4C:
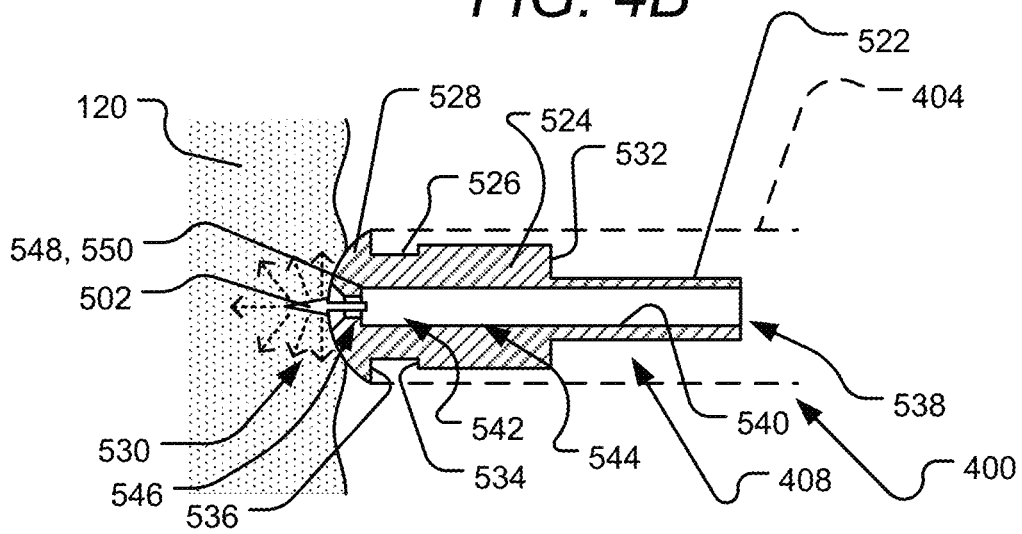

As shown in FIGS. 4A-4C, the electrode 408 is disposed at a distal end of the lead 400. A tubular lead body 404 of the lead 400 surrounds and secures the electrode 408 within the lead 400 and is shown in broken line to clearly depict the electrode 408. As can be understood from FIG. 4A, the electrode 408 may include a generally cylindrical body of various diameters including a proximal cylindrical body 522, a central cylindrical body 524, a distal cylindrical body 526, and a distal tip 528 in the form of a partially spherical surface tapering inward to a distal opening 530. A proximally facing surface 532 separates the proximal cylindrical body 522 and the central cylindrical body 524. And a distal facing surface 534 separates the central cylindrical body 524 and the distal cylindrical body 526. A proximally facing surface 536 separates the distal tip 528 and the distal cylindrical body 526. The tubular lead body 104 grips the body of the electrode 408 so as to secure it in position without permitting fluid to enter a space between the electrode 408 and the lead body 404.

The electrode 408 further includes a proximal opening 538 and an inner surface 540 defining a lumen 542 that extends to the distal opening 530. That is, the lumen 542 extends fully through the electrode 408. The inner surface 540 of the electrode 408 includes a proximal cylindrical section 544, a distal cylindrical section 546, and a shoulder 548 having a proximally facing surface 550 separating the two sections 544, 546. The distal opening 530 expands as it extends and transitions to the distal tip 528.

As seen in FIG. 4A, the placement stylet 520 includes a stylet body 552 that may terminate in a ball end 554. The stylet body 552 may extend proximally through the lead and may be manipulated by the user to position the lead within the heart. As seen in FIG. 4A, the placement stylet 520 may be positioned within the lumen 542 of the electrode 408 such that the ball end 554 of the stylet 520 abuts the proximally facing surface 550 of the shoulder 548 on the inner surface 540 of the electrode 408. That is, the stylet 520 does not fully pass through the electrode 408. In this way, the placement stylet 520 may be used to deliver the lead through the heart and in particular to advance the lead tip or electrode 408 to a desired position within the heart (e.g., abutting the myocardium) as seen in FIG. 4A.

Following placement of the electrode 408 at an implantation site, such as the myocardium 120, the placement stylet 520 may be withdrawn from the tubular lead body 404 of the lead 400. Next, as seen in FIG. 4B, the delivery stylet 500 coupled with the MCRD 502 may be inserted into the tubular lead body 404 of the lead 400, and advanced until the distal facing surface 510 of the shoulder 508 of the delivery stylet 500 (or a similar feature, each of the distal facing surface 510 and the shoulder 508 being indicated in FIG. 3) abuts the proximally facing surface 550 of the shoulder 548 on the inner surface 540 of the electrode 408 (or a similar feature). In this position, the distal stylet end 506 extends through the distal cylindrical section 546 of the electrode 108 with the MCRD 502 extending distally beyond a distal-most point of the distal tip 528 of the electrode 408 and into the tissue of the myocardium 120. It is noted that an insertion depth may be limited by the length of the distal stylet end 506 as the stylet 500 can only extend up until it makes contact with the proximally facing surface 550 of the shoulder 548 on the inner surface 540 of the electrode 408.

Next, as seen in FIG. 4C, which is the same cross-sectional side view of the electrode 408 and myocardium 120 of FIGS. 4A and 4B, the delivery stylet 500 may be proximally retracted, leaving the MCRD 502 implanted in the tissue of the myocardium 120. Following implantation, the MCRD 502 elutes an active agent, such as a steroid, to surrounding tissue as indicated by the arrows surrounding the MCRD 502 in FIG. 4C.

Although not fully illustrated in FIGS. 4A-4C, it should be understood that the lead body 404 generally defines a lumen extending from a proximal portion of the lead 400 to the proximal opening 538 of the electrode 408 through which the delivery stylet 500 may be inserted. The lead body 404 may further include coiled wire or other electrical transmission means disposed along or about the lumen to enable electrical connection between the electrode 408 and other electrical components of the lead 400 (e.g., a shock/defibrillation coil, sensing coils, etc.) and a connector assembly of an implantable device, such as a pulse generator.

A physician may opt for a MCRD 502 with a particular shape, configuration, and/or material for the particular procedure. As an example, the physician may elect a MCRD 502 made from a resorbable polymer with a particular ratio of monomers in the polymer that yield a resorption time that is suitable for the procedure and optimizes the physiological effect. Additionally, or alternatively, the physician may elect a MCRD 502 with a particular shape, such as the shapes and configurations shown and described with reference to FIGS. 6A-6F.

In certain instances, the MCRD 502 may be utilized independently of the electrode 408. For example, a physician may opt for delivery of an electrode 408 without subsequent delivery of a MCRD 502. Such instances may include, without limitation, cases where the patient may have an intolerance to a particular active agent. The electrode 408 may nevertheless permit a subsequent implantation of an MCRD 502 in a subsequent procedure.

In another instance, the electrode 408 may be repositioned after initial implantation. For example, following an initial implantation procedure including delivery of a first MCRD, a physician may determine that adequate pacing is not being achieved or that there is some other factor affecting the performance of the lead. Such cases may not be detected until well after (e.g., days or weeks) the initial implantation of the lead. With a conventional electrode design, such as shown in FIGS. 1A-1C, the entire lead must generally be removed from the patient in order to replace the original MCRD (which would be partially or entirely depleted) with a new MCRD. Alternatively, in cases where the MCRD is sealed within the lead and cannot be removed/replaced, the initial lead may need to be replaced in its entirety with a new lead including a new MCRD. In either case, the lead including a new MCRD or a new lead must then be reinserted into the heart for implantation at a new pacing location.

In contrast to the foregoing conventional approach, implementations of the present disclosure enable relocation of the electrode 408 and provision of a new MCRD 502 without requiring removal of the lead 400 from the patient. More specifically, the electrode 408 may be dislodged from the initial implantation site and relocated to a new implantation site. Once at the new implantation site, a new delivery stylet 500 including a new MCRD 502 may be used to deliver a new MCRD 502 to the new implantation location. Accordingly, the electrode 408 may be relocated and a new MCRD 502 may be provided at the new implantation site without the time, complexity, and costs associated with fully removing a lead, replacing an MCRD of the lead (or the entire lead if the MCRD cannot be removed/replaced), and delivering the lead to the new implantation location, among other things.

At least certain implementations of the present disclosure may facilitate a reduced rigid length of the implantable lead as compared to conventional leads. By reducing the rigid length—particularly at the tip of the lead—the lead becomes easier to manipulate and place within the heart (or other implantation location) and, as a result, may lead to improved implantation accuracy, reduced implantation time, and other similar benefits. Moreover, the reduced rigid length of the lead may enable implantation of the lead in areas of the heart that are better for pacing but ultimately unreachable or unavailable when using conventional leads having longer rigid lengths.

The foregoing improvement is illustrated in further detail in FIGS. 5A and 5B. More specifically, FIGS. 5A and 5B illustrate a conventional electrode 108 and an electrode 408 in accordance with the present disclosure, respectively. The conventional electrode 108 of FIG. 5A includes a distal chamber 114 for housing an MCRD 118. The conventional electrode 108 further defines a proximal opening 112 that terminates proximal the distal chamber 114 and into which a placement stylet 150 may be inserted to facilitate delivery and implantation of the conventional electrode 108. In contrast, the electrode 408 of FIG. 5B defines a lumen 542 fully passing through the electrode 408. As previously discussed in the context of FIG. 4A, during delivery and implantation of the electrode 408, the placement stylet 520 is made to abut a shoulder 548 disposed just proximal the distal opening 530 of the electrode 408. As shown in FIG. 5B, the shoulder 548 also provides a stop for the delivery stylet 500 during delivery of the MCRD 502. As seen in FIG. 5A, a length L1 of the conventional electrode 108 from a distal tip 152 to a proximal end 154 is longer than a length L2 of the electrode 408 of FIG. 5B extending between the distal tip 528 and the proximal end 556. More specifically, the electrode 108 of FIG. 5A slidingly couples with the placement stylet 150 only through a portion of the proximal end of the electrode 108 since the distal chamber 114 is sealed from the distal opening 112. Accordingly, the length of the conventional electrode 108 is at least as long as the length of the distal chamber 114 and the proximal opening 112, combined. In contrast, the electrode 408 of FIG. 5B, includes a lumen 542 fully extending through the electrode 408 for an instrument (e.g., placement stylet, delivery stylet) to be positioned up to the shoulder 548 on the inner surface 540 of the electrode 408. Accordingly, the length of the electrode 408 is generally based on providing sufficient electrode length to be received and retained within a lead body (e.g., the lead body 404 of FIGS. 4A-4C) and/or to provide sufficient contact surface between the surface of the lumen 542 and the delivery stylet 500 so as to provide stability for the delivery stylet 500 during MCRD delivery. Stated differently, the omission of at least the distal chamber 114 from the electrode 408 allows for the overall length of the electrode 408 to be reduced, resulting in the various benefits, including the specific benefits noted above.

C. Example Active Agent Delivery Component Configurations

FIGS. 6A-6F illustrate six exemplary cross-sectional side views of active agent delivery components/MCRDs for use with the cardiac lead system described herein. In each figure, the MCRD 502A-502F is coupled with the distal stylet end 506 of the delivery stylet 500 in an interference fit or friction fit arrangement whereby the MCRD 502A-502F is capable of sliding out from within the distal bore 512 upon the MCRD 502A-502F being anchored to the tissue of the heart. Each MCRD 502A-502F of FIGS. 6A-6F includes a distal head 514 designed to anchor into the tissue of the heart and a tang 518 extending proximally from the distal head 514. The MCRD 502A of FIG. 6A includes a distal head 514 in the form of a conical surface that terminates at a penetrating tip 516. The distal head 514 also includes a proximal radial edge 558 and a planar proximally facing surface extending from the radial edge 558 to the tang 518. The MCRD 502A of FIG. 6A also includes a radiopaque marker in the form of an embedded radiopaque bead 503 embedded therein. As previously discussed, such markers may be included in any MCRD disclosed herein and may take various forms including, without limitation, embedded beads, strips, bands, or similar objects or radiopaque additives included when molding the MCRD.

Figure 6B:
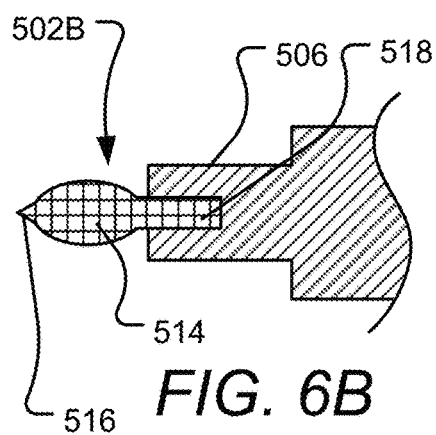

The MCRD 502B of FIG. 6B includes a bulbous distal head 514 in the form of an ellipsoid that terminates at a penetrating tip 516. A widest portion of the bulbous head 514 is about halfway along its length with the head 514 tapering inwardly in both distal and proximal directions. The MCRD 502C of FIG. 6C is similar to the MCRD 502A of FIG. 6A, except the MCRD 502C of FIG. 6C includes an intermediate cylindrical body 560 positioned between the tang 518 and the distal head 514. In this way, the proximal radial edge 558 is spaced apart from the end of the distal stylet end 506 to permit additional anchoring between the MCRD 502C and the tissue of the heart. The MCRD 502D of FIG. 6D includes a distal head 514 in the form of a conical surface that terminates at a penetrating tip 516. The distal head 514 is coupled to a cylindrical body 562 that is about the same diameter as the distal stylet end 506. The cylindrical body 562 includes a proximal radial edge 558 and a planar proximally facing surface extending from the radial edge 558 to the tang 518.

Figure 6E:
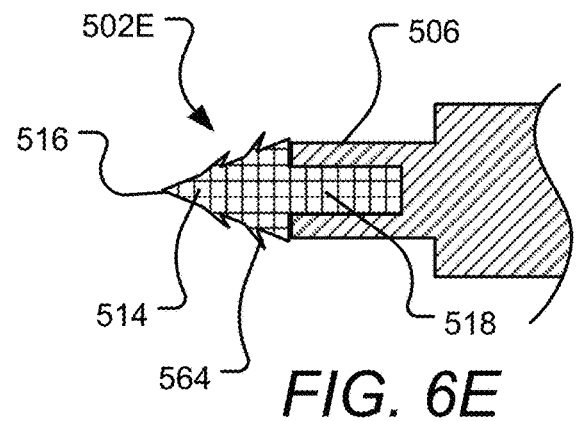
Figure 6C:
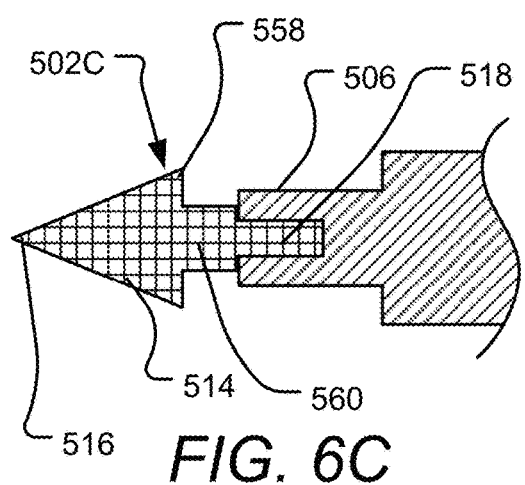
Figure 6F:
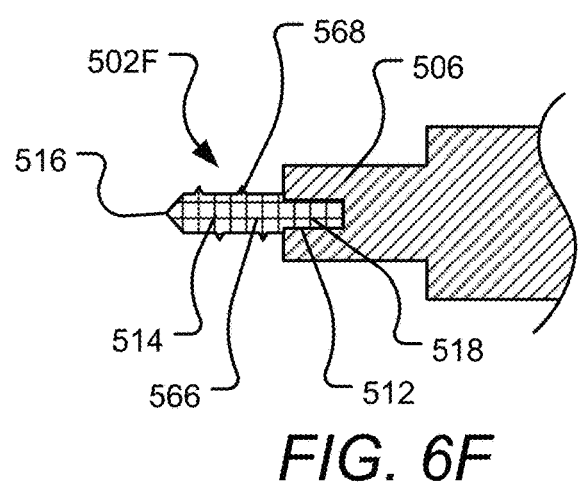

The MCRD 502E of FIG. 6E is similar to the MCRD 502A of FIG. 6A, except the MCRD 502E of FIG. 6E includes barbs 564 on the conical surface of the distal head 514 to facilitate anchoring to the tissue of the heart. The MCRD 502F of FIG. 6F includes a generally cylindrical body 566 and a helical thread 568 wrapping around the body 566. The cylindrical body 566 terminates at a distal tip 516. The tang 518 may be keyed so as to be non-rotational within the distal bore 512. In this way, the delivery stylet 500 may be rotated within the lead body 104 so as to rotationally advance the MCRD 502F into the tissue of the heart.

Each of MCRD 502A-502F should be regarded as examples of active agent delivery components/MCRDs that may be used in implementations of the present disclosure as well as illustrating certain features that may be included or combined in an MCRD. Accordingly, features of the foregoing MCRD designs may be used alone or in combination. Moreover, while specific examples of MCRDs are provided herein, implementations of the present disclosure are not limited to any specific shapes or configurations disclosed herein. More generally, any MCRD shape or configuration may be used in implementations of the present disclosure provided that the shape/configuration facilitates each of coupling to and deployment from a distal end of a delivery stylet, including implantation in tissue to be treated using the MCRD.

D. Example Coupling and Release Mechanisms

Figure 7A:
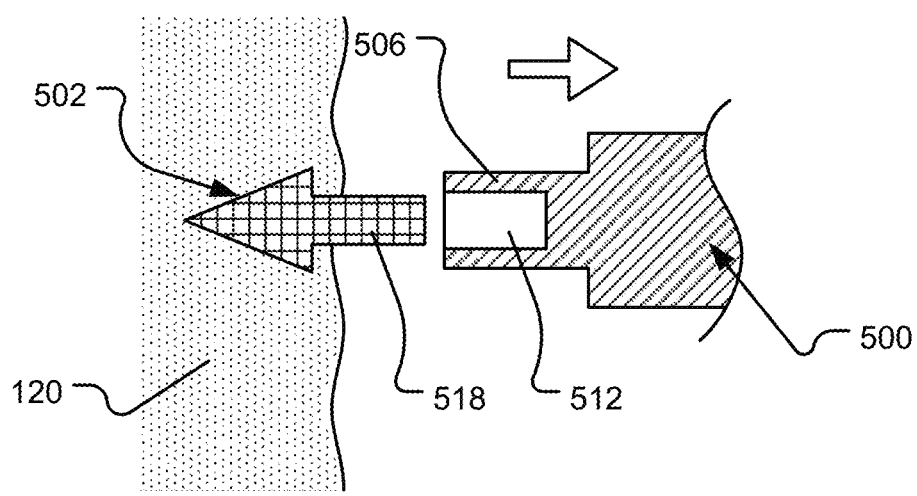
FIGS. 7A-7D are cross-sectional side views of a delivery stylet illustrating various structures for releasably coupling an active agent delivery component to a distal stylet end of the delivery stylet.

FIGS. 7A through 7D depict four exemplary ways for decoupling of the MCRD 502 and the distal stylet end 506 of the delivery stylet 500. These figures do not show the electrode 408 or other components of the lead system for clarity. To begin, FIG. 7A depicts a side cross-sectional view of the delivery stylet 500 and the MCRD 502, which is positioned within the myocardium 120. In this instance, the delivery stylet 500 is proximally retracted from the MCRD 502 via pulling after implantation of the MCRD 502. The pulling overcomes the friction-fit arrangement between the tang 518 of the MCRD 502 and the distal bore 512 of the distal stylet end 506 of the delivery stylet 500, thereby releasing the MCRD 502 from the delivery stylet 500.

Figure 7B:
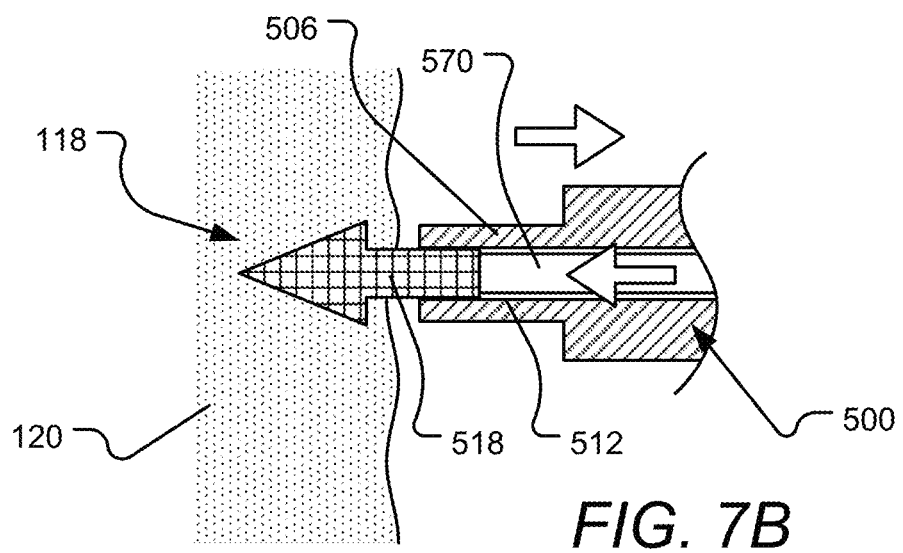

FIG. 7B depicts a side cross-sectional view of the delivery stylet 500 decoupling with the MCRD 502. As seen in the figure, the distal bore 512 of the stylet 500 is a full through-bore extending the length of the delivery stylet 500.

A push stylet 570 may be distally advanced within the delivery stylet 500 to push against the tang 518 of the MCRD 502 and to force the MCRD 502 into the myocardium 120. Pushing of the MCRD 502 by the push stylet 570 overcomes the friction-fit arrangement between the tang 518 of the MCRD and the distal bore 512 of the distal stylet end 506. In certain implementations, the friction-fit may be further or alternatively overcome by retracting the delivery stylet 500 while simultaneously pushing against the MCRD 502 or maintaining the MCRD 502 in position using the push stylet 570.

Figure 7C:
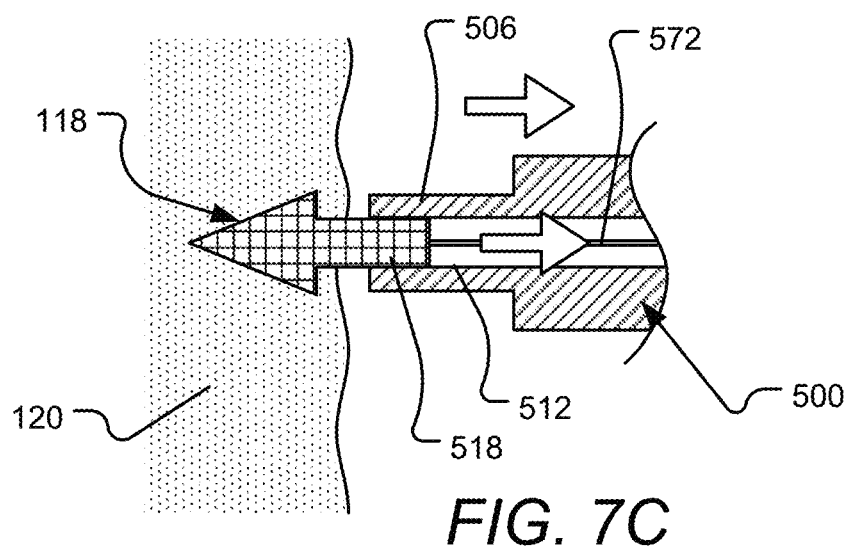

FIG. 7C depicts a side cross-sectional view of the delivery stylet 500 decoupling with the MCRD 502. As seen in the figure, a retention member 572 in the form of a breakable wire (e.g., formed of the MCRD 502 material or otherwise) is coupled to the tang 518 of the MCRD 502. Upon implantation of the MCRD 502 in the myocardium 120 the delivery stylet 500 and the retention member 572 may be retracted proximally. The proximal force will then sever the retention member 572 leaving the MCRD 502 anchored within the myocardium 120. As with the delivery stylet 500 of FIG. 7B, the stylet 500 in FIG. 7C may include a full through-bore within which the retention member 572 may be disposed.

Figure 7D:
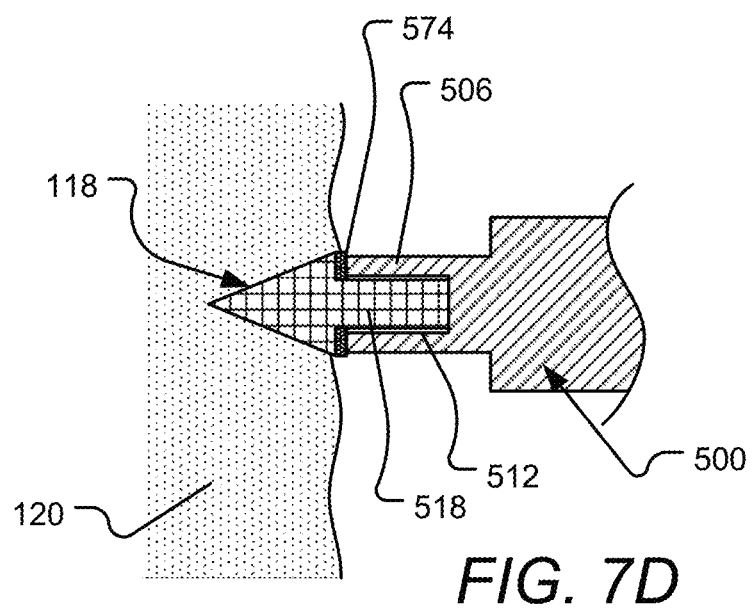

FIG. 7D depicts a side cross-sectional view of the delivery stylet 500 coupled with the MCRD 502, which is positioned in the myocardium 120. As seen in the figure, the annular tip of the distal stylet end 506 is coupled to the proximally facing surface of the MCRD 118 via a biocompatible chemical bonding material 574. The chemical bonding material 574 may dissolve upon interaction with the blood and/or bodily tissue/fluids in the myocardium 120. In at least certain implementations, the diameter of the distal bore 512 may be slightly larger than that of the tang 518, relying primarily on the chemical bonding material 574 to retain the MCRD 118 within the distal stylet end as opposed to the friction-fit arrangement in the previously described embodiments.

E. Delivery Using a Lead Tip with Active Fixation

Section II.B., above, described a cardiac lead system utilizing a lead tip or electrode 408 that was fixed to the myocardium via passive fixation members, e.g., fixation members that were not part of the electrode 408 but that were part of the tubular lead body 404 of the lead 400. In this section, the cardiac lead system described herein includes active fixation members, i.e., fixation members that both fix the lead to the myocardium and provide sensing and/or stimulation functionality.

Figure 8A:
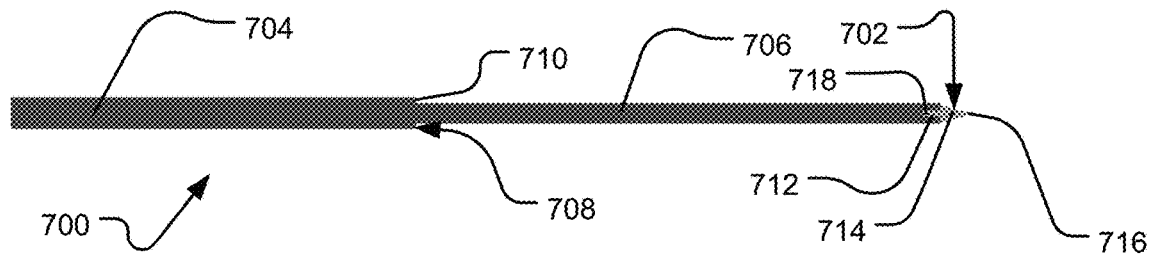
FIG. 8A is a side view of a delivery stylet coupled with an active agent delivery component, such as an MRCD.

To begin, reference is made to FIGS. 8A-8E. FIG. 8A depicts a cross-sectional side view of a delivery stylet 700 coupled to an active agent delivery component, such as an MCRD 702. As can be understood from FIG. 8A, the delivery stylet 700 may include a proximal stylet body 704 in the form of a cylindrical rod and a distal stylet end 706 in the form of a cylindrical rod that couples with the MCRD 702. As shown, the distal stylet end 706 may include a cylindrical body of a lesser diameter than a diameter of the stylet body 704. As a result, the delivery stylet 700 includes a shoulder 708 having a distal facing surface 710 defined by the junction of the distal stylet end 706 and the stylet body 704. The distal stylet end 706 may include a distal bore 712 for receiving a portion of the MCRD 702. The distal bore 712 may be defined centrally within the cylindrical body of the distal stylet end 706.

As seen in FIG. 8A, in one embodiment, the MCRD 702 may include a distal head 714 in the form of a conical distal surface that terminates at a piercing tip 716. And a tang 718 extending proximally from the distal head 714 for receiving in the distal bore 712 of the distal stylet end 706 of the delivery stylet 700. As previously discussed and as further discussed below, various shapes and configurations of the MCRD 702 are contemplated as are mechanisms to facilitate coupling and decoupling of the MCRD 702 to the distal stylet end 706, including mechanisms to facilitate deployment/implantation in cardiac tissue.

Figure 8B:
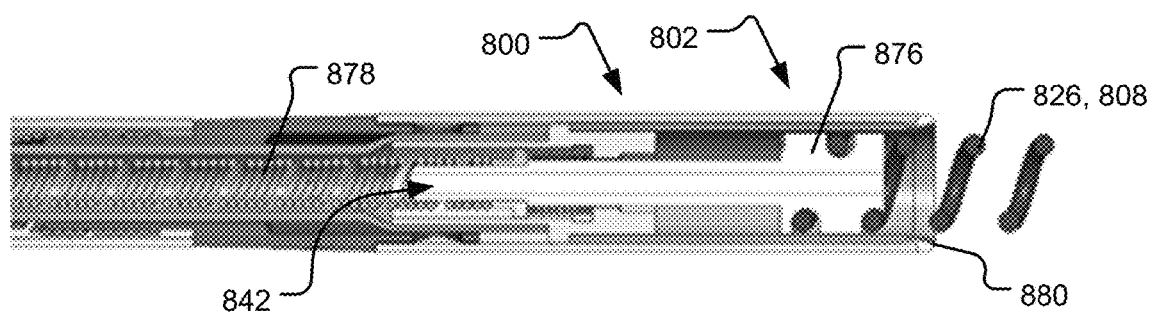
FIGS. 8B-8E are cross-sectional side views of a distal region of a lead with an active fixation anchor/electrode in various stages of delivery of an active agent delivery component using a delivery stylet.

FIGS. 8B-8E depict cross-sectional side views of a distal region 802 of an implantable cardiac lead 800. As illustrated in FIG. 8B, the distal region 802 includes a fixation anchor 826 that further acts as an electrode 808. The fixation anchor 826 is coupled to and supported within the lead 800 by a conductive post 876 or similar structure that is in turn coupled to conductive wires 878 extending along the lead 800, e.g., from a proximal lead connector assembly, such as the connector assembly 318 of FIG. 2A. Accordingly, an electrical pathway exists between the proximal end of the lead 800 (e.g., the connector assembly 318) and the fixation anchor/electrode 826, 808, thereby facilitating delivery of electrical impulses to the anchor/electrode 826, 808 and/or sensed electrical impulses from the anchor/electrode 826, 808.

During implantation, the lead 800 is inserted into and navigated to an implantation site, e.g., an implantation site within or on an exterior surface of a patient's heart. The anchor/electrode 826, 808 is then rotated (e.g., by rotating the lead 800 as a whole or an independently rotatable shaft within the lead 800 (not shown)) to engage the anchor/electrode 826, 808 with the cardiac tissue 890, such as shown in FIG. 10C. Once initially engaged, additional rotation of the anchor/electrode 826, 808 may be performed to further embed the anchor/electrode 826, 808 into the tissue 890.

Figure 8C:
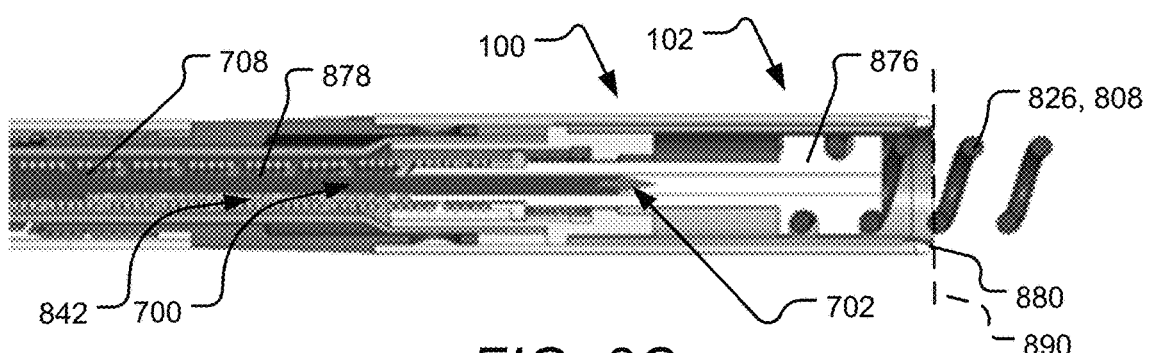
Figure 8D:
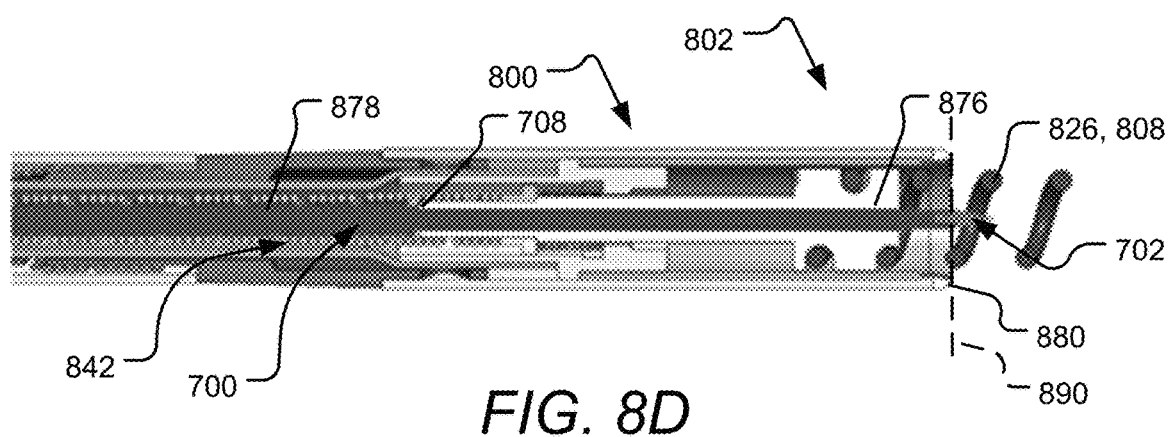
Figure 8E:
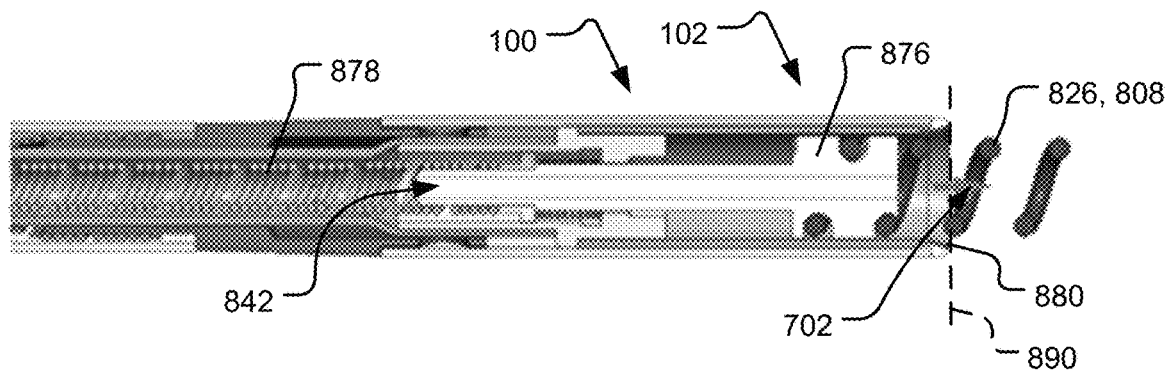

As further illustrated in FIG. 8C, following implantation of the lead 100 using the anchor/electrode 826, 808, the delivery stylet 700 including the MCRD 702 may be inserted into and distally advanced within the lead 800. Alternatively, the delivery stylet 700 may be disposed within the lead 800 during implantation of the anchor/electrode 826, 808 and subsequently moved distally following implantation of the anchor/electrode 826, 808. To facilitate movement of the delivery stylet 700 within the lead 800, the lead 800 generally defines a lumen 842 extending through the conductive wires 878, the conductive post 876, and the anchor/electrode 826, 808. The delivery stylet 700 and coupled MCRD 702 may therefore be advanced through the lumen 842 until the shoulder 708 contacts a proximal end of the conductive post 876, as shown in FIG. 8D. In this position, the MCRD 702 extends past the distal annulus 880 of the lead 800, and into the tissue 890 at the implantation site. Next, the delivery stylet 700 may be proximally retracted and removed, as seen in FIG. 8E, leaving the MCRD 702 within the tissue 890.

F. Delivery Stylet with Movable Inner Stylet

Figure 9A:
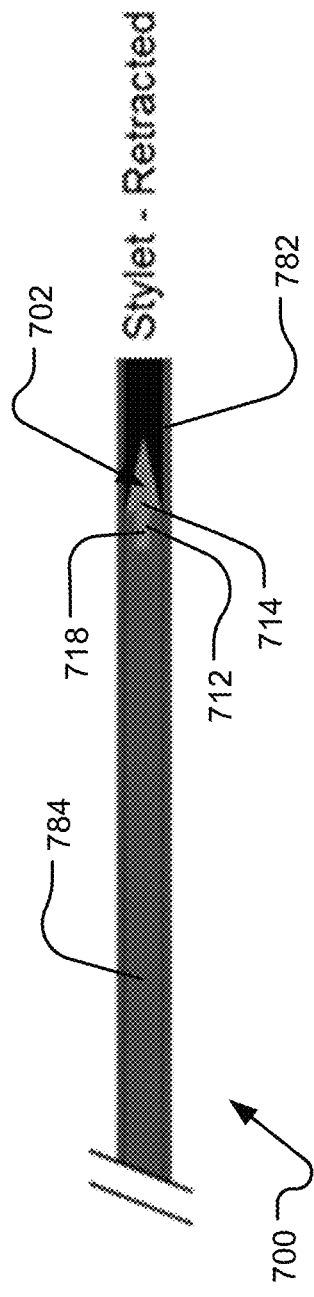
FIGS. 9A and 9B are, respectively, cross-sectional side views of a two-part delivery stylet coupled with an active agent delivery component in a retracted state and a deployed state.
Figure 9B:
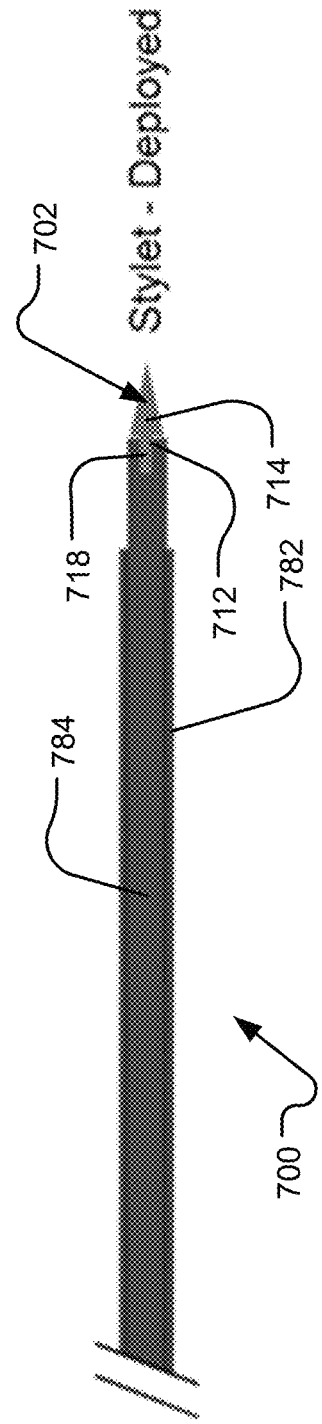

In certain implementations, the delivery stylet 700 of FIG. 8A (or any other delivery stylet disclosed herein) may be alternatively constructed with an outer sleeve 782 and an inner stylet 784, as seen in FIGS. 9A and 9B. As seen in FIG. 9A, which is a cross-sectional side view of the delivery stylet 700, the inner stylet 784 may slide within the outer sleeve 782, and may include a distal bore 712 defined therein for releasably coupling to the MCRD 702. FIG. 9B, which is also a cross-sectional side view of the delivery stylet 700 of FIG. 9A, illustrates how the inner stylet 784 may extend beyond the annulus of the outer sleeve 782 so as to extend the MCRD 702.

Figure 10A:
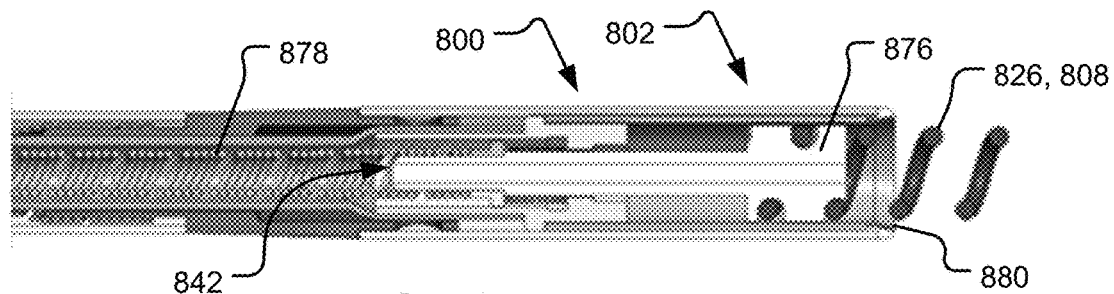
FIGS. 10A-10D are cross-sectional side views of a distal region of a lead with an active fixation anchor/electrode in various stages of delivery of an active agent delivery component using a two-part delivery stylet.
Figure 10B:
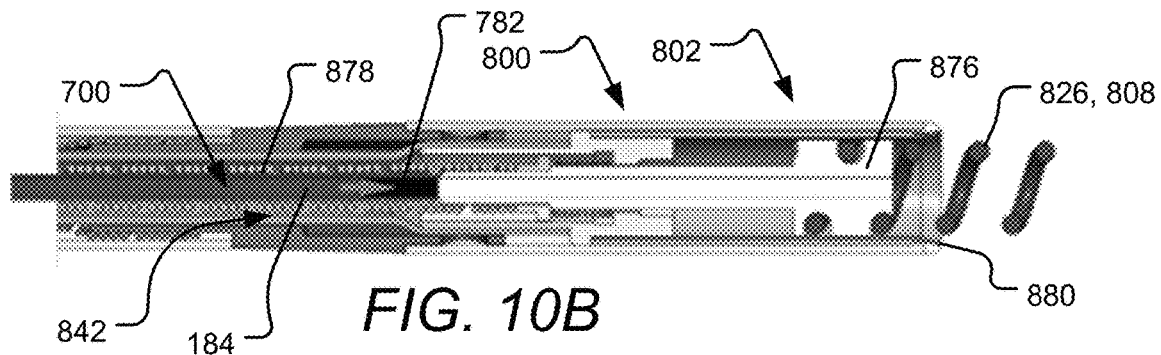
Figure 10C:
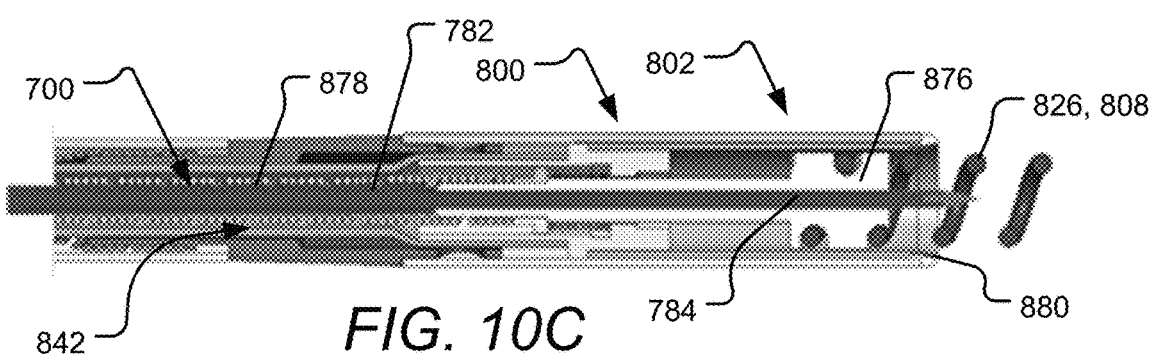

Use of the delivery stylet 500 of FIGS. 9A and 9B is illustrated in FIGS. 10A-10D, which depict cross-sectional side views of a distal region 802 of the implantable cardiac lead 800 previously discussed in the context of FIGS. 8A-8E. FIG. 10A depicts the distal region 802 of the cardiac lead 800 prior to introduction of the delivery stylet 700. In FIG. 10B, the outer sleeve 782 of the delivery stylet 700 is shown as being advanced within the lumen 842 of the lead 800 until the distal end of the outer sleeve 782 contacts a proximal portion of the conductive post 876. In at least certain instances, in this configuration, the outer sleeve 782 may be used to advance the distal region 802 of the lead 800, similar to the placement stylets discussed previously herein.

Figure 10D:
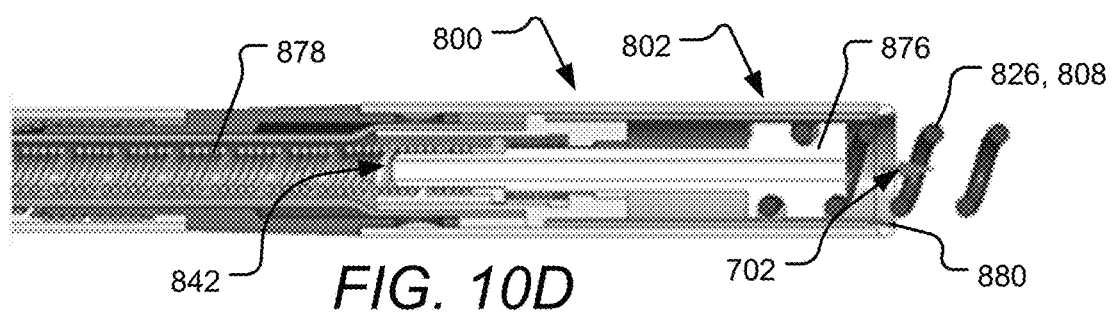

Next, as seen in FIG. 10C, the inner stylet 784 may be advanced through the outer sleeve 782, through the lumen 842 of the conductive post 876, and out of the lead 800. Doing so extends the MCRD 702 out of the distal end of the lead, e.g., into the tissue at the implantation site. Next, the inner stylet 784 and the outer sleeve 782 may be proximally retracted, as seen in FIG. 10D, leaving the MCRD 702 in place in the tissue at the implantation site.

Although illustrated in FIGS. 10A-10D as being used with an active fixation lead, delivery stylets including multiple sleeves, such as the delivery stylet 700 of FIGS. 9A and 9B may also be configured for use with passive fixation leads, such as those discussed in the context of FIGS. 4A-5D. For example, referring to FIG. 4B, following implantation of the lead and during delivery of the MCRD 702, the outer sleeve 782 of the delivery stylet 700 may be made to abut the proximally facing surface 550 of the shoulder 548 of the electrode 408. Subsequently, the inner stylet 584 may be translated distally to deliver/implant the MCRD 702. Alternatively, the outer sleeve may be made to abut any other proximally facing surface of the electrode prior to distal translation of the inner stylet 584.

III. Exemplary Method of Implanting a Cardiac Lead Tip and Active Agent Delivery Component FIG. 11 is a flowchart showing an exemplary method 1100 of implanting a cardiac lead tip into tissue at an implantation site, including implanting an active agent delivery component/MCRD at the implantation site.

As seen in FIG. 11, the method 1100 may include, at step 1102, implanting a distal lead end of a lead body into tissue, such as the myocardium. The lead body generally includes a distal lead and defines a lead lumen extending through the lead body to the distal lead end. In certain implementations, the distal lead end may be an active fixation distal lead end, such as a helical fixation anchor that also functions as an electrode and discussed above in the context of FIGS. 8B-8E and 10A-10D. Alternatively, the distal lead end may include a passive fixation anchor (e.g., tines, barbs jutting out from the tubular lead body) with a separate electrode fitted to the lead body and that abuts against the tissue when implanted, e.g., as seen in FIGS. 4A-4C, and 5B.

Next, at step 1104, the method 1100 may include inserting a delivery stylet through the lead lumen. The delivery stylet may include a stylet body having a distal stylet end and an active agent delivery component (e.g., an MCRD) detachably coupled to the distal stylet end. The delivery stylet may be a single piece or multi-piece stylet, as described above.

Step 1106 of the method 1100 may include extending the distal stylet end distally from the distal lead end such that the active agent delivery component is inserted into the tissue at the implantation site. Step 1108 of the method 1100 may include detaching the active agent delivery component from the distal stylet end and within the tissue at the implantation site. Detaching of the active agent delivery component may be done a variety of ways. For example, and without limitation, any of the release mechanisms and techniques described above in the context of FIGS. 7A-7D, 8E, and 10D may be used to detach the active agent delivery component within the tissue.

At step 1110, the delivery stylet may be fully retracted and removed from the lead body. Subsequent to removal of the delivery stylet, a proximal connector assembly of the lead may be inserted into or otherwise connected to an IPG or similar implantable device to electrically connect the electrode of the lead to the internal implantable device circuitry, thereby enabling pacing and/or sensing via the lead.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A system for use in delivery of active agents to a lead implantation location, the system comprising:
   a lead comprising:
      a lead body defining a lead lumen; and
      a distal lead end adapted to engage tissue, the lead lumen extending a length from a proximal region of the lead to a distal region of the lead and through the distal lead end; and
   a delivery stylet insertable through the lead lumen and including a stylet body having a distal stylet end, the distal stylet end detachably coupled to an active agent delivery component via one or more of a friction fit, a severable retention member, or a chemical bond that is dissolvable in organic bodily material,
   wherein the distal stylet end is configured to protrude from the distal lead end with the active agent delivery component coupled to the distal stylet end, thereby enabling insertion of the active agent delivery component into the tissue to which the distal lead end is engaged, and wherein the lead lumen is configured to permit the delivery stylet to move the active agent delivery component along the length of the lead lumen.

2. The system of claim 1, wherein the lead is a cardiac pacing lead and the distal lead end comprises a pacing electrode.

3. The system of claim 1, wherein the delivery stylet comprises a first feature configured to abut a second feature disposed within the lead lumen to limit each of distal movement of the delivery stylet within the lead lumen and protrusion of the delivery stylet from the distal lead end.

4. The system of claim 1, wherein the delivery stylet comprises:
   an outer sleeve; and
   an inner stylet movable within the outer sleeve, the inner stylet comprising the distal stylet end and the active agent delivery component.

5. The system of claim 1, wherein the stylet body defines a stylet lumen configured to receive a push tool for applying a force on the active agent delivery component.

6. The system of claim 1, wherein the active agent delivery component comprises a steroid.

7. A method of delivering active agents to tissue at an implantation location of a lead, the method comprising:
providing a lead including a lead body defining a lead lumen, the lead including a distal lead end configured to engage tissue at an implantation location, the lead lumen extending a length from a proximal region of the lead to a distal region of the lead and through the distal lead end;
inserting a delivery stylet through the lead lumen, the delivery stylet including a stylet body having a distal stylet end that is detachable coupled to an active agent delivery component via one or more of a friction fit, a severable retention member, or a chemical bond that is dissolvable in organic bodily material, wherein the lead lumen is configured to permit the delivery stylet to move the active agent delivery component along the length of the lead lumen;
extending the distal stylet end from the distal lead end such that the active agent delivery component is inserted into the tissue at the implantation location; and
detaching the active agent delivery component from the distal stylet end and within the tissue at the implantation location.

8. The method of claim 7, wherein:
the delivery stylet includes a distally facing surface and the lead includes a proximally facing surface disposed within the lead lumen; and
extending the distal stylet end from the distal lead end comprises abutting the distally facing surface with the proximally facing surface such that the active agent delivery component is extended a predetermined distance from the distal lead end.

9. The method of claim 7, wherein detaching the active agent delivery component from the distal stylet comprises at least one of:
retracting the stylet body after insertion of the active agent delivery component in the tissue at the implantation location;
inserting a push tool through the stylet body to apply a proximal force on the active agent delivery component; or
dissolving the chemical bond between the active agent delivery component and the distal stylet end.

10. A stylet for use in delivery of active agents to an implantation location of an implantable medical lead, the stylet comprising:
a stylet body having a distal stylet end, the stylet body defining a bore at the distal stylet end; and
an active agent delivery component detachably coupled to the distal stylet end via one or both of a severable retention member or a chemical bond that is dissolvable in organic bodily material, wherein a portion of the active agent delivery component is disposed within the bore while the active agent delivery component is coupled to the distal stylet end.

11. The stylet of claim 10, wherein the stylet body comprises:
an outer sleeve; and
an inner stylet movable within the outer sleeve, the inner stylet comprising the distal stylet end and the active agent delivery component.

12. The stylet of claim 10, wherein the stylet body comprises a distally facing surface disposed proximal the distal stylet end.

13. The stylet of claim 10, wherein the active agent delivery component comprises a radiopaque marker.

14. The stylet of claim 10, wherein the active agent delivery component is coupled to the distal stylet end by the chemical bond.

15. The stylet of claim 10, wherein the stylet body defines an inner lumen and the active agent delivery component is detachable from the distal stylet end by inserting an elongate tool through the inner lumen and applying a distal force on the active agent delivery component.

16. The stylet of claim 10, wherein the stylet body defines an inner lumen and further comprises an elongate retention tool disposed within the inner lumen and coupled to the active agent delivery component, the active agent delivery component being detachable from the distal stylet end by retracting the elongate retention tool.

17. The system of claim 1, wherein the delivery stylet defines a bore at the distal stylet end, and a portion of the active agent delivery component is disposed within the bore while the active agent delivery component is coupled to the distal stylet end.

18. The system of claim 17, wherein the active agent delivery component includes a distal head and a tang that extends from the distal head, and the tang is the portion of the active agent delivery component that is received in the bore of the delivery stylet.

19. The stylet of claim 10, wherein the active agent delivery component includes a distal head and a tang that extends from the distal head, wherein the active agent delivery component is coupled to the stylet body via the severable retention member that extends between the tang and the delivery stylet.

* * * * *